(12) United States Patent
Bec et al.

(10) Patent No.: US 7,911,670 B2
(45) Date of Patent: Mar. 22, 2011

(54) FLUORESCENCE-BASED SCANNING IMAGING DEVICE

(75) Inventors: Daniel Bec, Villeneuve-Tolosane (FR); Vincent Paveau, Vernet (FR); Stephane Le Brun, Carbonne (FR)

(73) Assignee: Innopsys, Carbonne (FR)

( * ) Notice: Subject to any disclaimer, the term of this patent is extended or adjusted under 35 U.S.C. 154(b) by 212 days.

(21) Appl. No.: 12/092,767

(22) PCT Filed: Nov. 7, 2006

(86) PCT No.: PCT/EP2006/068184
§ 371 (c)(1),
(2), (4) Date: Oct. 8, 2008

(87) PCT Pub. No.: WO2007/054495
PCT Pub. Date: May 18, 2007

(65) Prior Publication Data
US 2009/0218513 A1  Sep. 3, 2009

(30) Foreign Application Priority Data

Nov. 9, 2005 (FR) ........................................ 05 53401

(51) Int. Cl.
G02B 26/10 (2006.01)
(52) U.S. Cl. .................... 359/221.2; 359/196.1; 359/393
(58) Field of Classification Search .............. 359/196.1, 359/221.2, 391–394
See application file for complete search history.

(56) References Cited

U.S. PATENT DOCUMENTS

| | | | | |
|---|---|---|---|---|
| 3,778,621 A * | 12/1973 | Mikajiri | ................... | 250/442.11 |
| 3,826,558 A * | 7/1974 | Rasberry et al. | .............. | 359/393 |
| 4,744,642 A * | 5/1988 | Yoshinaga et al. | ............ | 359/379 |
| 4,948,330 A * | 8/1990 | Nomura et al. | ................ | 414/754 |
| 5,323,712 A * | 6/1994 | Kikuiri | ............................ | 108/20 |
| 5,459,325 A * | 10/1995 | Hueton et al. | ............. | 250/458.1 |
| 5,583,691 A * | 12/1996 | Yamane et al. | ................ | 359/393 |
| 6,137,627 A * | 10/2000 | Engelhardt et al. | ........... | 359/393 |
| 6,407,858 B1 * | 6/2002 | Montagu | ....................... | 359/391 |
| 7,095,032 B2 * | 8/2006 | Montagu et al. | ........... | 250/458.1 |
| 2003/0173509 A1 * | 9/2003 | Ito et al. | ......................... | 250/235 |
| 2004/0066552 A1 * | 4/2004 | Werba | ........................... | 359/391 |
| 2004/0075879 A1 * | 4/2004 | Karin | ............................ | 359/212 |

FOREIGN PATENT DOCUMENTS

| | | | |
|---|---|---|---|
| JP | 04053917 A | * | 2/1992 |
| JP | 04063314 A | * | 2/1992 |

* cited by examiner

Primary Examiner — Mark Consilvio
(74) Attorney, Agent, or Firm — Perman & Green, LLP

(57) ABSTRACT

A device for analysing a specimen by fluorescence includes a confocal microscope, illumination means capable of emitting a light beam that converges, by means of an objective, on a focal spot, means for successively positioning the focal spot at various points on the specimen during analysis. The confocal microscope includes an objective mounted on a movable rapid-scan carriage driven in a reciprocating linear movement along a traverse direction by a rotating motor by means of a device of the connecting rod type. The specimen is placed on a movable support driven in a longitudinal movement and is able to move along the axis of the objective of the microscope in order to position the specimen relative to the focal spot. The excitation light spectrum is spread over the surface of the specimen in such a way that the excitation light reflected by the specimen and corresponding to the wavelengths close to fluorescence converge on points that are sufficiently distant from a diaphragm positioned in front of a device for measuring the fluorescence.

19 Claims, 7 Drawing Sheets

FLUORESCENCE-BASED SCANNING IMAGING DEVICE

CROSS REFERENCE TO RELATED APPLICATIONS

This application is the National Stage of International Application No. PCT/EP2006/068184, International Filing Date, 7 Nov. 2006, which designated the United States of America, and which International Application was published under PCT Article 21 (2) as WO Publication No. WO2007/054495 and which claims priority from French Application No. 0553401, filed on 9 Nov. 2005, the disclosures of which are incorporated herein by reference in their entireties.

BACKGROUND

1. Field

The disclosed embodiments relate to a fluorescence imaging device such as those used in fluorescence analysis of biochips. More specifically, the disclosed embodiments relate to means for ensuring the various movements necessary in the course of the analysis in order to scan the surface of a chip point by point by locating each point, during its analysis, in the focal plane of a confocal microscope.

2. Brief Description of Related Developments

The analysis of the deoxyribonucleic acid, or DNA, of living organisms is of major importance in modern biology, as much for advancing knowledge of biological mechanisms as for detecting certain illnesses associated with faults in cell function.

A widespread technique for analyzing a DNA sample consists in producing biochips that are analyzed by means of fluorescence techniques.

The production of biochips is known. Its essential steps consist in depositing samples of DNA fragments to be studied on a lamella, in mixing these samples with separately prepared targets consisting of DNA labeled with fluorochromes, i.e. molecules that emit light by fluorescence when they are themselves excited by an energy source, especially excitation light, and in hybridizing the DNA to be studied with the labeled DNA. In the course of the hybridization, some strands of labeled DNA will couple with their complementary sample of DNA to be studied and thus render the strands of the DNA studied that correspond to the labeled DNA detectable by fluorescence.

The fluorochromes may be of several types and more often than not dyes that are fluorescent in red light, the dye called Cy5, or in green light, the dye called Cy3, are used.

Generally, many samples are deposited on a biochip, which constitute an array of rows and columns at the intersection of which the samples to be analyzed are found. A sample represents a "patch" or "spot" of around 50 micrometers in diameter and on a biochip carried by a traditional microscope lamella, typically 26 mm wide by 75 mm long, around 30 000 spots are frequently found.

To analyze such biochips use is made of reading devices that illuminate the samples of the biochip point by point and record the fluorescence response of each point to provide a fluorescence map of the biochip. To detect the fluorescence response at the scale of the sample DNA strand, it is necessary for the reading device to have a resolution of around 10 micrometers or less.

There are such reading devices that employ a microscope called a "confocal" microscope and a scanning system that enables the surface of the biochip to be read in a reasonable time while analyzing this surface point by point.

The confocal microscope is an optical microscope often coupled with fluorescence techniques that uses monochromatic light (most often coming from a laser source) to illuminate the sample and observe the response of said sample through a pinhole, which has the effect of practically limiting the area of the sample observed to the focal plane of the objective, often less than 2 micrometers deep, and to confer on the microscope a high resolution close to the theoretical maximum for a microscope using photons in the visible region. To compensate for the loss in luminosity due to the small opening of the pinhole, observation is carried out by means of a photomultiplier, the measurements of which are recorded in order to reconstruct the images of the sample observed point by point by conventional imaging means, for example on a computer.

The very low depth of field intrinsic to the confocal microscope makes it necessary, during its use to read chips, to control the position of the focal point of the microscope in order that the area illuminated by the excitation laser and its fluorescent response be correctly positioned despite irregularities in the surface of the chip and the uncertainties in the position of this surface.

To control the position of the focal point, the known imaging devices use active control means to control the lens or the group of lenses of the microscope objective. This lens or group of lenses is mounted in a movable manner and its position is permanently adjusted along the optical axis of the objective by an actuator such as a magnetic coil or a piezoelectric actuator in response to a focusing error signal. This movable assembly is particularly fragile and sensitive to impacts and is likely to be disturbed.

To read all the points of the chip successively and reconstruct a fluorescence image of each of the samples to be analyzed, the chip is subjected to scanning by the focal point of the confocal microscope.

Conventionally, the surface of the chip is scanned along its transverse axis by means of rapid displacement of the objective of the confocal microscope and the chip support moves at a lower speed along a perpendicular axis, the longitudinal axis, so that the objective describes a series of approximately parallel reading lines, until the entire surface of the chip has been scanned. In some models of biochip analyzer, the objective of the microscope is carried by a carriage guided on rails along a straight path, moved by a linear motor as described for example in the U.S. Pat. No. 5,459,325 or moved by a rotating motor by means of a connecting rod assembly as shown by the figures of the Patent JP 2003 185583. In other models, such as for example described in the U.S. Pat. No. 6,201,639, the microscope objective is carried by an arm undergoes an oscillating rotational movement about a vertical axis and describes a path in a circular arc above the biochip.

This type of mounting of the microscope objective proves to be relatively expensive to produce due to the cost of the components themselves, such as that of the linear motors, or due to the complexity of the movements in order to obtain a constant scanning rate. The complexity of these elements is also increased when the means of focusing the confocal microscope objective are mounted on the movable part, which increases the mass thereof.

Furthermore, the delicate focusing means linked to the microscope objective must take account of the fact that the objective is movable and is subject to frequent accelerations each time the scanning changes direction.

SUMMARY

The disclosed embodiments propose solutions to these various problems which improve the performance of the imaging device in an economical manner.

To position and maintain the sample point in the course of analysis at the focal point in a precise manner, in particular as is necessary when the device uses a confocal microscope, without making use of movable optical elements, the scanning imaging device for scanning the surface of a sample comprises:

optical means determining a focal point;
a device for displacing the focal point in a rapid scanning movement, in a direction X approximately parallel to the surface of the sample, in order to describe at least one scanning line along X at the surface of the sample;
a movable support on which the sample is fixed; and
a device for displacing said movable support in a direction Y, approximately parallel to the surface of the sample and approximately perpendicular to the rapid scanning direction X.

The movable support rests on guiding columns in Y that leave said movable support free to move in a Z direction approximately perpendicular to the plane defined by the X and Y directions.

At least one first actuator displaces the movable support in relation to the optical means in the Z direction such that the scanning line along X is shifted approximately uniformly in the Z direction.

At least one second actuator modifies the inclination of the movable support in such a way that the scanning line along X is essentially inclined in a plane defined by the X and Z directions by rotation about a rotation axis, called the roll axis, the position of which varies depending on the position of the movable support along the Y axis and/or depending on the position determined by the first actuator of the movable support in the Z direction.

To permanently maintain the focal point at the desired distance from the sample, despite imperfections of the sample surface and of the mechanism for moving the optical means for scanning in the X direction, a focus control device generates a focal point position error signal and, in response to said error signal, during the rapid scanning movement along X, controls the first actuator to correct the position of the surface of the sample by acting on the position on the Z axis of the scanning line at the surface of the sample.

In order to reduce the errors in position along a scanning line and to limit the amplitudes and the corrections of Z position, the focus control device controls the second actuator during the rapid scanning movement along X to change the inclination of the scanning line along X and to permanently reestablish the parallelism between the line described by the focal point and the surface of the sample for the line being analyzed.

The second actuator is advantageously controlled at a lower frequency than the frequency at which the first actuator is controlled to take account of the more long-term action of said second actuator.

In order to produce actuators at low cost and to generate little friction on the movable support, the actuators each comprise at least one roller with an axis of rotation that is off-center in relation to the axis of a motor used to change the Z position of the axis of rotation of the roller.

In order to act to the first order on the Z distance between the focal point and the sample, the roller of the first actuator, called the height roller, acts on the movable support at a point of action lying approximately in a plane defined by the X and Z directions and by the scanning line along X, and preferably on a point of action lying approximately on the axis of the sample in the Y direction when the point of action lies on one face of the movable support.

To act to the first order on the inclination of the sample, the roller of the second actuator, called the roll roller, acts on the movable support at a point of action distant from the roll axis and preferably offset in the X direction in relation to the point of action of the first actuator when the latter acts directly on the movable support.

To ensure the stability of the movable support and to be able to adjust the device to limit the corrections to be carried out by the focusing device, the movable support rests on a fixed, or preferably adjustable, support element offset in the Y direction in relation to a line passing through the points of action of the first actuator and of the second actuator. Said support element, together with the point of action of the first actuator, determines the roll axis.

In one particular embodiment of the device which leads to simplified kinematics of the movements of the movable support, the first actuator, for modifying the position of the movable support in the Z direction, acts through a displacement in the Z direction of a point of action applied to one face of a guiding structure on which the movable support is movable in the Y direction. In this case, the second actuator advantageously acts on a point of action applied to one face of the movable support, offset in the X direction in relation to a guiding column joined to the guiding structure and allowing rotation of the movable support about an axis approximately parallel to the Y direction.

Advantageously, the device employs a confocal microscope the distance of which from the focal point in relation to the sample must be permanently adjusted in a precise manner.

The rapid scanning movement in the X direction is advantageously obtained by a displacement along a linear path of the optical means, in relation to which the Z position of the sample is adjusted, in particular in an alternating movement in which the optical means are driven by a rotating motor and a connecting rod joined in an offset manner to an output shaft of said motor, which enables scanning at high speeds, permitted by the focusing device, with simple and inexpensive means.

The device is applied to imaging the surface of a sample by stimulating the fluorescence of the sample.

In this case, in order to increase the signal-noise ratio of the image by using economical optical stimulation sources, for example a laser diode, with an insufficiently monochromatic emission spectrum, the fluorescence is stimulated by at least one light source having an intensity peak centered on a wavelength $\lambda_0$ shifted in relation to the fluorescence wavelength, said device comprising:

an optical dispersion means, such as an arrangement of prisms, which guides the light radiation corresponding to the various wavelengths emitted by the light source in different directions;
an optical means, such as a set of lenses, that causes radiation from the light source corresponding to the wavelength $\lambda_0$ to converge on the focal point;
a confocal microscope for observing the fluorescence emitted by the surface of the sample comprising a pinhole through the opening of which the light received by a photon sensor passes, said confocal microscope being set up so that the light coming from the surface of the sample close to the focal point, emitted by fluorescence, arrives at the pinhole opening and so that the light emitted by the source at wavelengths shifted in relation to $\lambda_0$ close to the wavelength of the fluorescence light, and reflected by the surface of the sample, from points on the surface of the sample offset in relation to the focal point, arrive alongside the pinhole opening and do not reach the photon sensor.

Advantageously, when the stimulation light source generates a beam of light with a cross section differing in size depending on the axis considered, the optical dispersion means is set up to obtain, by anamorphosis, a beam having approximately the same non-sectional size along the various axes.

In one embodiment, the fluorescence measurements are carried out with the position of the rapid scanning carriage or of the motor output shaft being servocontrolled by a sampling frequency FE such that the distance between two successive measurements is constant in order to obtain a fluorescence image of the surface of the biochip of approximately constant spatial resolution.

In another embodiment, the fluorescence measurements are carried out with the speed of the rapid scanning carriage or of the motor output shaft being servocontrolled by a sampling frequency FE such that the distance between two successive measurements is approximately constant.

In one particular embodiment, the rotation speed of the motor output shaft is variable in the measurement area such that the variations in speed of the rapid scanning carriage are reduced in relation to the case in which said output shaft has a constant rotation speed in order to limit the differences in illumination, due to different exposure times to the excitation light, between the various points measured.

For example, the speed of displacement along X of the rapid scanning carriage is made approximately linear over the measurement area by acting on the rotation speed of the motor.

This result is obtained, for example, with a rotation speed of the motor output shaft depending on a frequency proportional to the sampling frequency FE of fluorescence measurements, or else by superposing on the supply signal a sinusoidal signal coming from a third-order harmonic, which has the effect of making the speed of the rapid scanning carriage approximately constant over a substantial part of its stroke along X.

The detailed description of an embodiment is provided with reference to the figures, which show:

Figure 1:
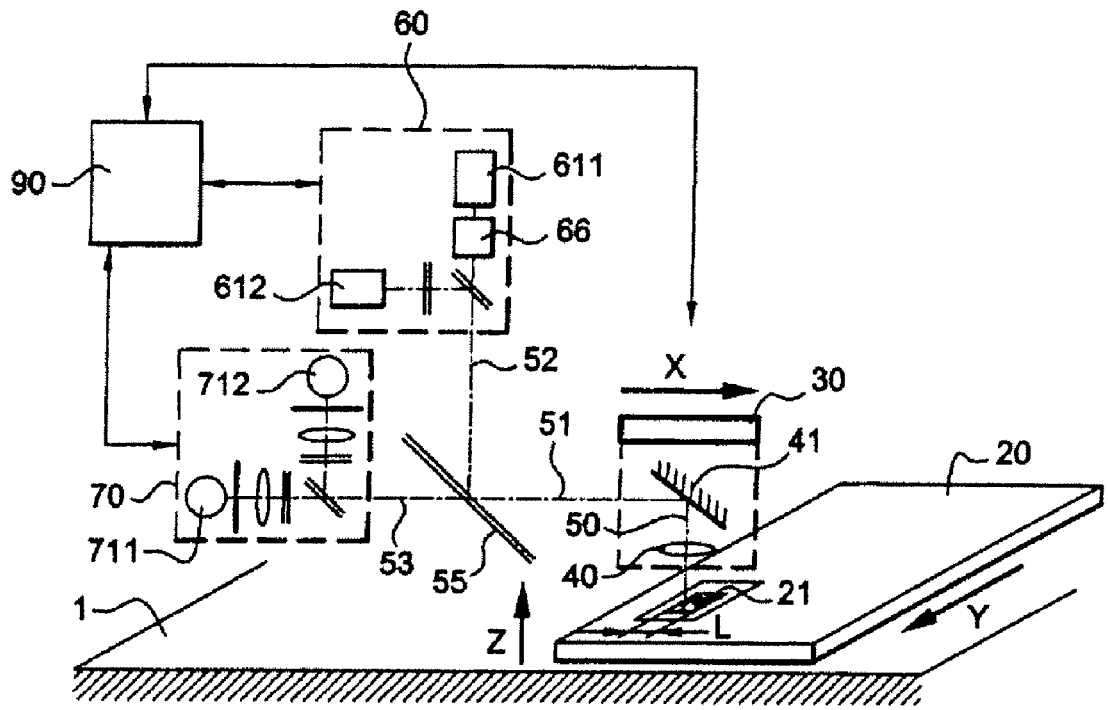
FIG. 1: general presentation of a biochip analysis scanning device and its main components.
Figure 2:
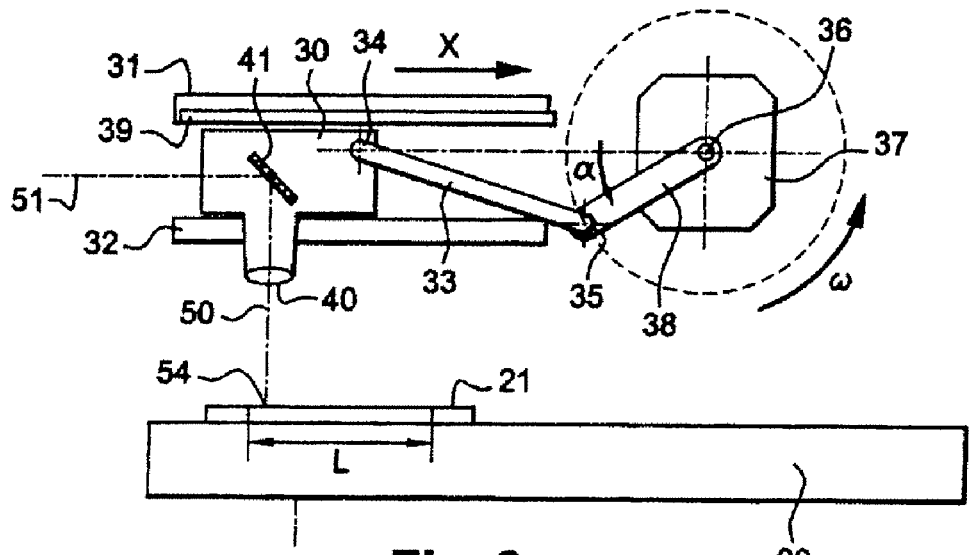
FIG. 2: principle of the device for rapid scanning along X by a carriage carrying the confocal microscope objective, driven in translation by a rotating motor.

A fluorescence imaging system, in particular for biochip analysis, according to the disclosed embodiments comprises means 20 for supporting a chip or a sample 21, a confocal microscope comprising means 60 for illuminating the chip and means 70 for measuring the fluorescence and an objective 40, means for scanning the chip 21 in the course of analysis by the objective 40, means for positioning a focal point 54 of the confocal microscope in relation to samples deposited on the chip 21 and means 90 for controlling the device, and for acquiring and processing fluorescence measurement signals.

The analysis of a chip 21 consists of a series of elementary measurements of the surface of the chip. An elementary measurement consists in acquiring the fluorescence intensity value for at least one given wavelength of the fluorescence and one point on the chip. In order to read successively all the points of the surface of the chip 21, the latter is positioned on a support 20, called the movable support, movable along a first axis called the longitudinal Y displacement axis, and is scanned by the objective 40 of the confocal microscope, carried by a carriage 30 fixed along the Y axis, movable along an axis approximately perpendicular to the Y axis called the transverse X displacement axis. The distance between the area being analyzed and the objective is kept approximately constant in the optical axis 50 of the objective 40. The chip 21 is held on the movable support 20 in such a way that the plane defined by the surface of the samples to be analyzed is approximately parallel to the plane defined by the two directions Y and X of displacement of the movable support 20 and the carriage 30 respectively.

The movable support 20, the total stroke of which in the Y direction is at least equal to the distance to be analyzed on the chip 21, in general several tens of millimeters, is guided, for example, by means of a guiding column 22, rigidly joined to a fixed support 10, on which the movable support 20 rests to follow a path parallel to the Y direction. A nut 23 is fixedly mounted mounted to the movable support 20 and is passed through by a fine thread screw 24. At the opposite end to the nut 23, the fine thread screw 24 is held to avoid translational movements of said screw relative to the fixed support 10, while allowing rotation about its axis, and is connected to a motor 25, for example an electric stepper motor, able to rotate the fine thread screw 24.

The rotation of the motor 25 turns the fine thread screw 24, which through its action on the nut 23 leads to translation along Y of the movable support 20 in relation to the fixed support 10.

The pitch of the screw 24, in combination with the angle of rotation of the motor 25 at each longitudinal displacement δY of the movable support 20 along the Y axis, is calculated to correspond to a displacement of the movable support 20 equal to the desired distance between two successive scanning lines in the X direction of the chip 21 by the objective 40 of the confocal microscope. Preferably, the movement of the movable support 20 is stopped during the scanning of a line along the X axis and, between two scans along the X axis, the movable support 20 is displaced in the Y direction, by means of rotation by a predetermined angle of the motor 25, by the desired distance δY between two consecutive lines of scanning along X.

Advantageously, in the course of an operation of completely scanning a chip, the movable support is always displaced along the Y axis in the same direction, for example pushed by the fine thread screw 24. By following this method of displacing the movable support 20, the functional play and/or or the play due to the assembly of the screw 24 and the other connections for mounting the nut 23 and the motor 25 have no effect on the precision of the displacement as the active forces are always applied in the same direction both in rotation and in translation. This method avoids the necessity of using a very precise screw and high-precision mountings.

The carriage 30 is mounted so as to be able to move along the X axis, approximately perpendicular to the Y displacement axis of the movable support 20 and approximately parallel to the surface of the movable support 20 that carries the chip 21. The carriage 30 is guided by means 31, 32 joined to a reference support 1 of the analysis device. The guiding means 31, 32 are determined so that the displacement of the carriage 30 along the X axis is possible over a distance at least equal to the width L of the surface to be analyzed of the chip 21, typically several tens of millimeters.

In a preferred embodiment, the carriage 30 is linked by a connecting rod 33, joined to one end 34 of said carriage 30, to an output shaft 36 of a rotary motor 36 in a manner offset by a distance D between the axis of the output shaft 36 of said motor and a joint 35 at the other end of the connecting rod 33, for example by means of a crank 38 or a disk. The motor 37 is fixedly mounted relative to the reference support 1. The axis of rotation of the output shaft 36 of said motor 37 is approximately perpendicular to the X displacement direction of the carriage 30 such that when the output shaft 36 turns, the carriage 30 held by the guiding means 31, 32 is driven in an reciprocating linear movement, the amplitude of which is defined by the geometric characteristics of the mounting. The axis of the output shaft 36 of the motor 37 preferably passes close to the axis defined by the joint 34 of the connecting rod 33 with the carriage 30 and the X displacement direction of the carriage so that the stroke of the carriage 30 is approximately equal to twice the distance D.

The objective 40 of the confocal microscope is fixedly mounted on the carriage 30. The optical axis of the objective 30 is approximately perpendicular to the plane defined by the directions of the displacements along X of the carriage 30 and along Y of the movable support 20, i.e. approximately in the plane of the surface of the chip 21 to be analyzed. Means 41 for optical reflection by 90° to the axis 50 of said objective, for example a mirror inclined at 45°, are located on the carriage 30 that the optical axis of the objective 40 is reflected 30 in such a way to be directed along an axis 51 so as in a direction parallel to the scanning axis X of the carriage 30. The means 60 for illuminating the chip 21 and the means 70 for sensing the fluorescence emitted are fixedly mounted to the reference support 2 in the optical axis 51 reflected by 90 degrees from the optical axis 50 of the objective.

When the movable support 20 is in a given longitudinal position on the Y axis, the carriage 30 carrying the objective 40 of the confocal microscope makes a rapid transverse movement along the X axis approximately perpendicular to the displacement along Y of the movable support 20 to cover the chip 21 along a line in the direction of its width. The carriage 30 is driven in this rapid scan by the connecting rod 33 actuated by the continuous rotation of the rotary motor 37. The offset D of the point of the joint 35 of the connecting rod 33 on the motor side is such that, when the shaft 36 of the motor 37 makes one revolution, the stroke C of the carriage 30 and hence of the objective 40 above the movable support 20 is at least equal to the width L of the area to be analyzed of the chip 21, i.e. C≧L.

The principle of driving the carriage 30 by connecting rod and crank leads to a progressive decrease in the velocity $V_c$ of translation of the carriage 30 before this velocity is reversed at the ends of the reciprocating stroke along the X axis. For example, if the rotation speed ω of the axis 36 of the motor 37 is constant, the velocity $V_c$ of the carriage follows an approximately sinusoidal curve as a function of time t of the type $V_c = D \sin(\omega t)$.

The variation in the velocity $V_c$ of rapid scanning along the X axis of the carriage 30, and hence of the objective 40 of the microscope, which is avoided in the known analyzers by the use of expensive linear motors, poses two types of problem.

First, the successive fluorescence measurements must be carried out approximately equidistantly over the chip 21 along a scanning line along the X axis in order to obtain an approximately constant spatial resolution for the image of fluorescence at the surface of the chip.

Second, the intensity of the fluorescence emitted by the fluorochromes is influenced by the quantity of light received and hence by the duration of the exposure to the illumination means 60 of the confocal microscope. Furthermore, the fluorochromes are rendered passive, at least partly, a phenomenon known by the name "bleaching", after they have been exposed to excitation light for the first time, i.e. they have lost part of their capacity to emit fluorescence light. Slowing the speed of scanning by the objective of the confocal microscope increases the amount of light energy received locally and may lead to sufficient illumination of areas of the sample neighboring that being analyzed in order to render said neighboring areas passive, at least partly, and distort measurements during later analysis of these neighboring areas.

Diverse solutions, implemented individually or in combination, can be used to avoid or reduce the intensity of these phenomena.

A first solution for preserving an approximately constant spatial resolution during the analysis of the surface of the chip 21 consists in making the sampling frequency FE of the fluorescence measurement dependent on the X position or on the velocity $V_c$ of the carriage 30 such that these measurements are equidistant over the chip 21. The position of the carriage 30 is measured, for example, by means of an optical rule, or is calculated as a function of the angular position of the output shaft 36 of the motor 37 measured by an angular sensor (not shown). Each time the carriage 30 has covered a given distance corresponding to the measurement pitch PM, a new fluorescence measurement is carried out. When the velocity $V_c$ of the carriage is used as a parameter, the sampling frequency FE is directly proportional to the instantaneous velocity $V_c$ of the carriage 30 and inversely proportional to the measurement pitch PM. With an equation $FE = kV_c$, the measurements at the surface of the chip 21 are separated by $PM = V_c/FE$ or $1/k$. In this embodiment, the value chosen for the stroke C of the carriage 30 is such that the velocity $V_c$ along X in the area of width L where the fluorescence measurements are carried out remains greater than a critical value, below which the effects of bleaching are no longer acceptable. The areas in which the velocity of the objective of the microscope is inevitably too low, i.e. at the ends of the stroke C of the carriage 30, are kept outside the area of width L in which the measurements are carried out.

Another solution consists in making the velocity $V_c$ of the carriage approximately linear over a significant amplitude of the stroke C of the carriage 30 by acting on the rotation speed ω of the motor 37, which is no longer constant. Thus the rotation speed ω of the motor 37 is a function of the position of the carriage 30 or of the angular position α of the output shaft 36 of the motor 37 such that the translation velocity $V_c$ of the carriage 30 is approximately constant when the objective 40 of the microscope is over the area of the chip 21 to be analyzed. At the ends of the stroke C of the carriage 30, for values of α close to 0 or to π, the velocity of the carriage 30 is reduced, in order to be cancelled when the direction of displacement reverses. The total stroke C of the carriage along the X axis is greater than the width of the area of the chip 21 that must be analyzed, so that the areas where the velocity of the carriage is no longer approximately constant are located outside the measurement area.

In a preferred embodiment, the motor 37 is a micro-pitch motor that is controlled by superposing a constant rotation speed and a rotation speed consisting of accelerations and decelerations.

In particular, by superposing a sinusoidal signal coming from a third-order harmonic on a constant rotation speed, hence a signal with a much lower energy than that corresponding to the constant rotation speed, the displacement speed of the carriage 30 is rendered sufficiently linear with regard to the precision sought over more than 90% of the stroke along X of the carriage. For example, for a stroke L of 23 mm the carriage has a total stroke C of only 27 mm, or 2 mm excess at each end of the stroke.

The action on the rotation speed ω of the output shaft 36 of the motor 37 allows the total stroke C of the carriage 30 to be reduced by limiting the stroke which cannot be used for the analysis and consequently the dimensions of the analysis device to be reduced, and when the displacement velocity $V_c$ of the carriage is sufficiently constant over the useful stroke of the movement along X, it is possible to use a constant sampling frequency FE to obtain approximately equidistant measurement points over the width L to be analyzed of the chip 21.

Another solution consists in rotationally driving the rotating motor 37 according to a law ω(t), synchronized with the sampling frequency FE of the confocal microscope, over the stroke L of the carriage 30 when situated in the measurement area so that the distance covered along X by the carriage 30 between two successive measurements is always the same. In this case, when the objective 40 of the microscope reaches the edge of the measurement area, the servocontrol by the sampling frequency is interrupted until the carriage 30 has reversed the direction of its movement and is once again above an area to be analyzed. During this interruption, the rotation speed ω of the output shaft 36 of the motor 37 is advantageously kept constant.

The illumination means 60 and the measurement means 70 for measuring the emitted fluorescence are assembled on the optical axis 51 oriented in the direction X of the rapid scanning movement of the movable carriage 30.

After passing through the objective 40, the light emitted by the illumination means 60 converges on a focal point 54 where the area to be analyzed must be located.

Following a reverse path, the light emitted by the area of the chip 21 in the field of the objective 40 is sent in the direction X along the optical axis 51 in the direction of the measurement means 70.

According to the principle of the confocal microscope, only the light emitted by a point 54 lying in the focal plane of the objective 40 is measured by the measurement means 70, and according to the device of the disclosed embodiments the distance of the focal point 54 is permanently adjusted in relation to the surface of the chip 21 during the scanning along X and along Y by means able to displace the movable support 20 of the chip.

Said means modify the position of the movable support 20 on which the chip 21 is fixed in a direction, called the height direction, along an axis Z approximately perpendicular to the plane defined by the axes of longitudinal displacement along Y and transverse displacement along X, i.e. approximately in the direction of the optical axis 50 of the objective 40 of the confocal microscope carried by the carriage 30 for rapid scanning along X.

Figure 3:
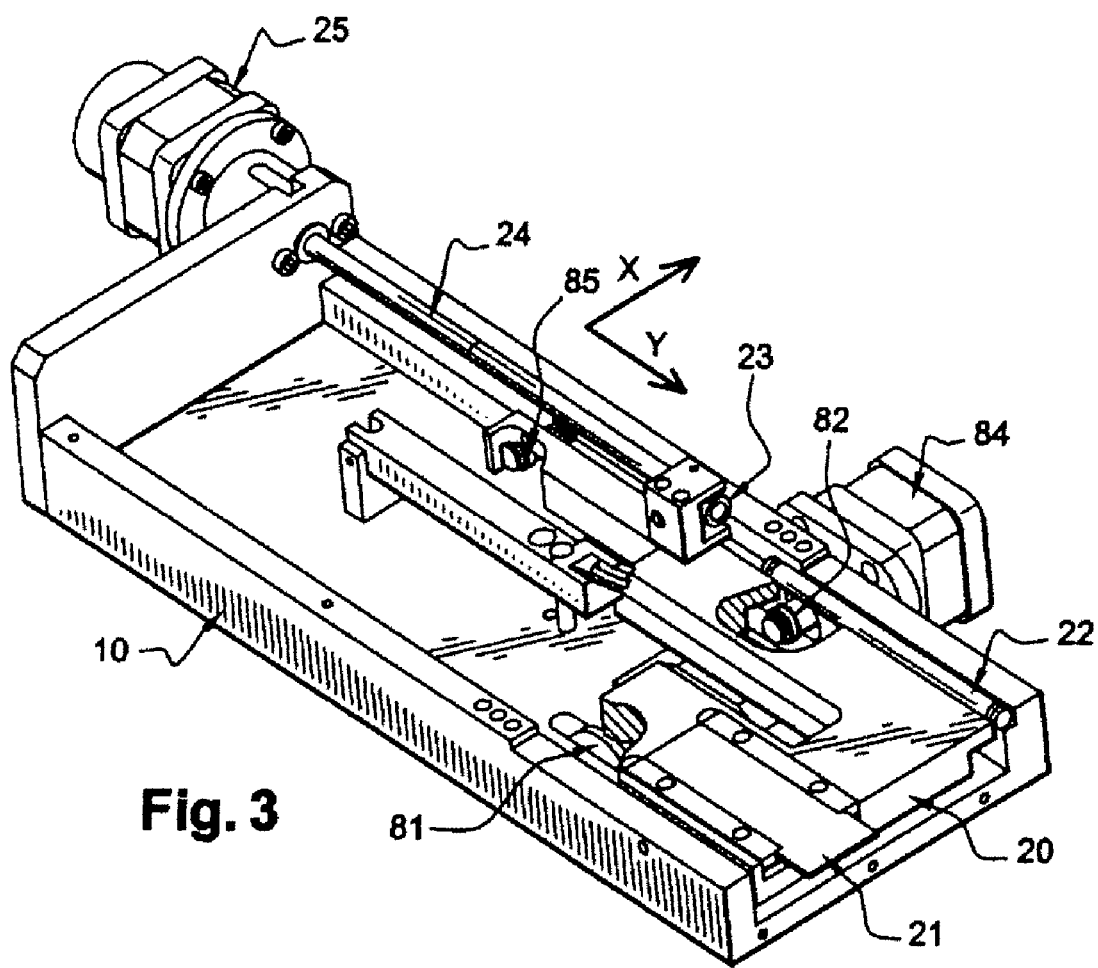
FIG. 3: perspective view from above of the movable support and the device for driving it in the Y direction, and of a first embodiment of focus adjustment means by movement along Z.
Figure 4:
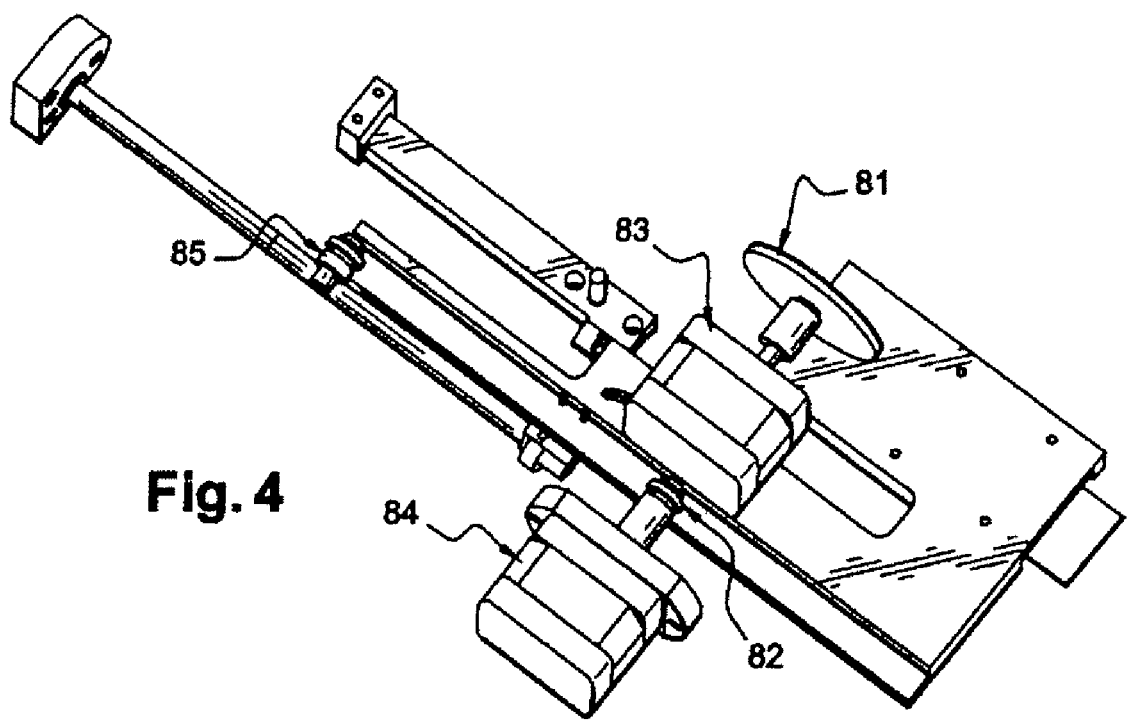
FIG. 4: view from below of the device of FIG. 3.

In a preferred embodiment shown in FIGS. 3 and 4, these means comprise two rollers 81, 82 spaced apart, in contact with which the movable support 20 is displaced. These rollers 81, 82 preferably have their axes perpendicular to the Y direction of displacement of the movable support 20 to facilitate the displacement thereof without needless wear or forces on the screw-nut assembly, and their points of action on the movable support 20 are approximately in the plane defined by the rapid scanning movement of the optical axis 50 of the objective 40 mounted on the carriage 30. The first roller 81 is positioned on the X axis close to the mean position of the optical axis 50, i.e. approximately on the longitudinal axis of the chip parallel to the Y displacement of the movable support. The second roller 82 is positioned laterally, for example close to the edge of the movable support 20 that is farthest from the axis of the chip 21. The Z position of the axis of each of the rollers 81, 82 can be modified, for example by mounting the roller axis on an eccentric shaft, said eccentric shaft being rotationally driven by respective motors 83, 84, for example micro-pitch motors, with which they respectively form actuators (81, 83) and (82, 84).

The action on the Z position of the axis of the first roller 81, situated close to the optical axis 50, modifies to the first order the distance between the chip 21 and the objective 40 of the microscope.

The action on the Z position of the axis of the second roller 82, offset in relation to the axis of the chip 21, modifies to the first order the lateral inclination of the movable support 20 of the chip, i.e. by inclining said chip by an angle called the roll angle about an axis approximately parallel to the Y direction passing through the point of contact of the first roller 81 with the movable support 20.

Servocontrol means (not shown) for controlling the Z position of the axis of the first roller 81 correct the focusing errors measured, for example, by an astigmatic sensor (not shown). These servocontrol means act during the analysis of the chip 21 on said first roller 81 so as to permanently adjust the Z position, close to the optical axis 50, of the movable support 20, with a relatively high frequency, for example with a frequency of around 30 hertz, in order to keep the focal point 54 over the area of the chip being analyzed. These servocontrol means furthermore act during the reading of the chip 21 on the second roller 82 to correct the roll angle. This correction minimizes the mean focusing error corrected by the first roller 81 in the course of a scanning along the X axis and hence limits the amplitude of Z corrections of the first roller 81.

The second roller 82 hence acts dynamically on a more long-term mean value, with a lower frequency than that of the first roller 81, for example a frequency of 3 hertz, correcting the inclination of the chip to keep the line scanned by the focal point 54 along the rapid scanning axis X approximately parallel to the path of the objective 40 carried by the carriage 30.

By thus decoupling the two functions of focusing along Z and of compensating for the inclination, only the means for correcting focus along Z associated with the first roller 81 need to be relatively high-performance.

Advantageously, the focusing means are set in the return area of the rapid scanning along X, i.e. in the area in which the focal point 54 is beyond the area of width L of the chip that is to be analyzed.

Advantageously, the fine thread screw 24 is driven by its motor 25 by means of a mounting 26 that is able to transmit the rotational movement of the motor to the screw even in the case of misalignment, for example a Cardan joint, in order that the means 23, 24, 25 for driving the movable support 20 in the Y direction operate satisfactorily with the Z movement of said movable support, even of low amplitude. Alternatively, the motor 25 and the fine thread screw 24 are assembled to preserve a permanent alignment and the motor is supported so as to be able to freely pivot about an axis (not shown) approximately parallel to the scanning direction X, under the effect of the oscillation movements of the fine thread screw 24 caused by the Z displacements of the movable support 20.

Secondarily, a third roller 85, offset in the Y direction in relation to the line defined by the points of contact of the first two rollers 81, 82, ensures the stability of the movable support 20 during its displacement along Y. This third roller 85 is preferably mounted on a fixed axis, the Z position of which can be adjusted when adjusting the analysis device so that the chip 21 on the movable support 20 is approximately perpendicular to the axis 50 of the objective 40.

Figure 5:
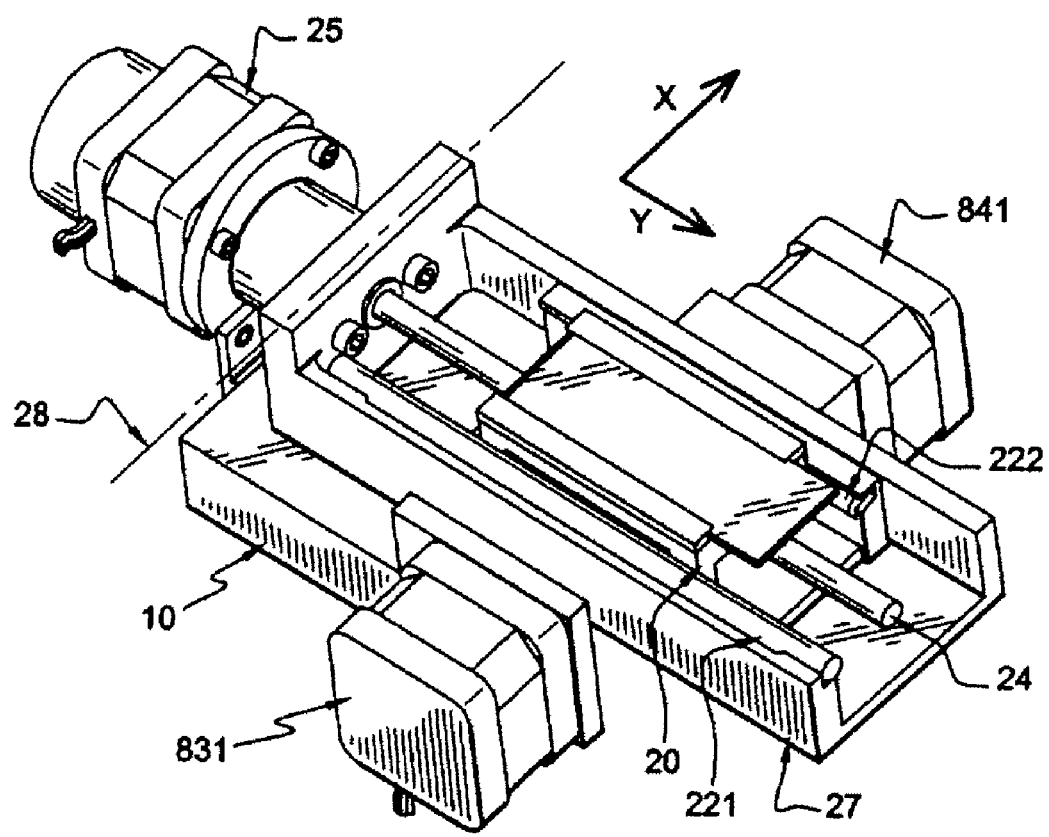
FIG. 5: perspective view from above of the movable support and the device for driving it in the Y direction, and of a second embodiment of focus adjustment means by movement along Z.
Figure 6:
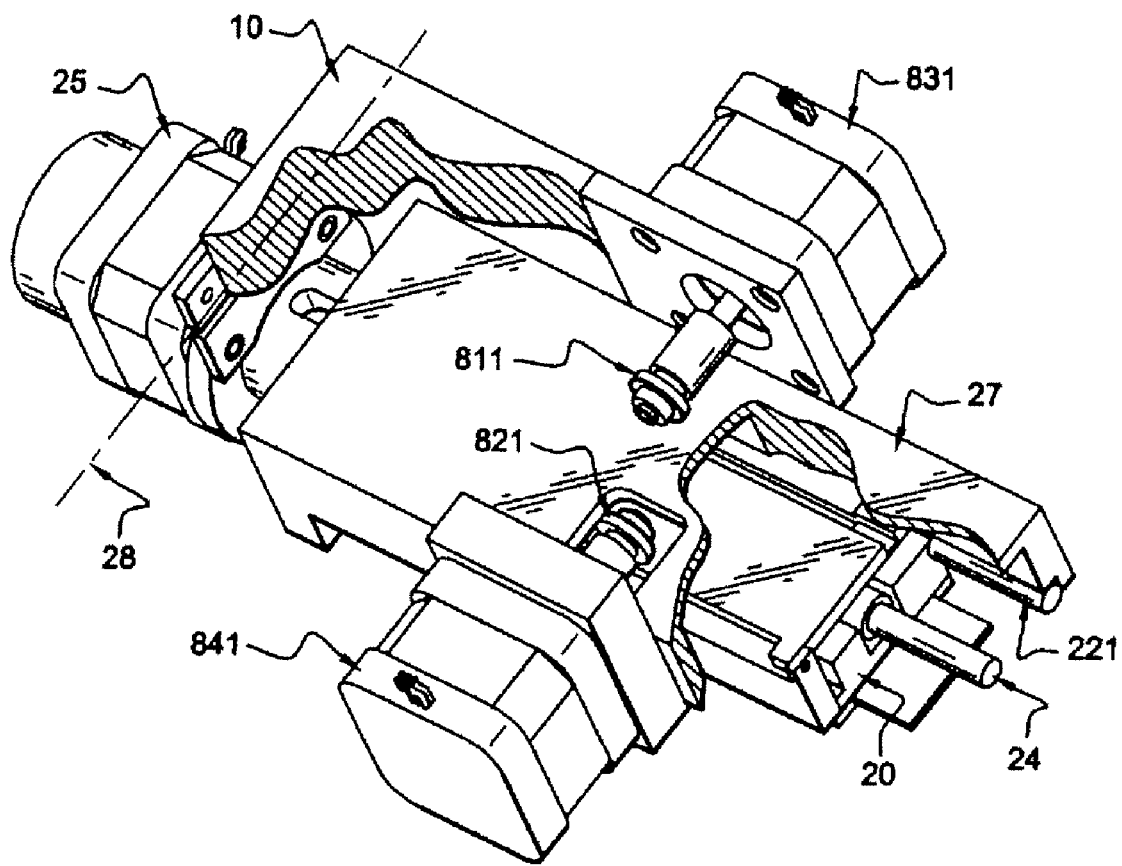
FIG. 6: view from below of the device of FIG. 5.

In an alternative solution corresponding to FIGS. 5 and 6, the movable support 20 is supported by two guiding columns 221, 222, against which they move. One of these columns 221 is fixed in relation to a guiding structure 27 and the other 222 is movable along Z in relation to said guiding structure, for example under the action of an eccentric roller 821 moved by a micro-pitch motor 841, with which it forms an actuator, such that the movable support 20 is inclined in relation to the guiding structure 27 under the action of the roller 821 about an axis parallel to the Y axis, which has the effect of modifying the inclination of the surface of the chip 21 in relation to the rapid scanning axis along X. Said guiding structure 27—which bears the guiding columns 221, 222, the movable support 20 and the eccentric roller 821 with its micro-pitch motor 841—pivots under the action of another eccentric roller 811 and moved by another micro-pitch motor 831, with which it forms another actuator, about an articulation axis 28, joined to the fixed support 10, parallel to the rapid scanning axis X and distant from the rapid scanning line at the surface of the chip 21 and from said other roller 811.

The micro-pitch motors 831, 841 are servocontrolled to correct the Z position and the inclination of the chip 21 respectively in response to an error signal given by a focusing sensor (not shown). As in the preceding embodiment, the motor 831 acting on the Z position is servocontrolled at high speed and the motor 841 acting on the inclination is servocontrolled at a relatively slow frequency. In a preferred embodiment, the motor 25 rotationally driving the fine thread screw 24 that displaces the movable support 20 in the Y direction is joined to the guiding structure 27.

The illumination means 60 necessary to stimulate the fluorescence comprise one or more light sources 611, 612 to illuminate the area of the chip 21, the fluorescence of which is analyzed.

This or these light source(s), generally gas or solid-state lasers, provide(s) light beams capable of being focused to produce a regularly shaped patch at the focal point 54, and furthermore the wavelength of the light emitted by each source is sufficiently different from that emitted by the fluorescence it causes for the light reflected by the surface of the chip 21 to be separated from the fluorescence before arriving at the sensor(s) 711, 712 for measuring fluorescence light. This latter result is all the more difficult to obtain satisfactorily as the luminous power emitted by the illumination means 60, typically a few tens of milliwatts, is several orders of magnitude greater than that emitted by the fluorescence, typically a few picowatts.

In one embodiment, at least one light source 611 of the analysis device according to the disclosed embodiments comprises a laser diode 64 as the light emitter.

Laser diodes constitute cheap laser sources, but have the defect of generating a divergent light beam with very different apertures depending on the emission plane. Furthermore, their emission spectrum is not purely monochromatic and spreads toward high wavelengths through to wavelengths that are difficult and expensive to eliminate through filters.

Figure 7:
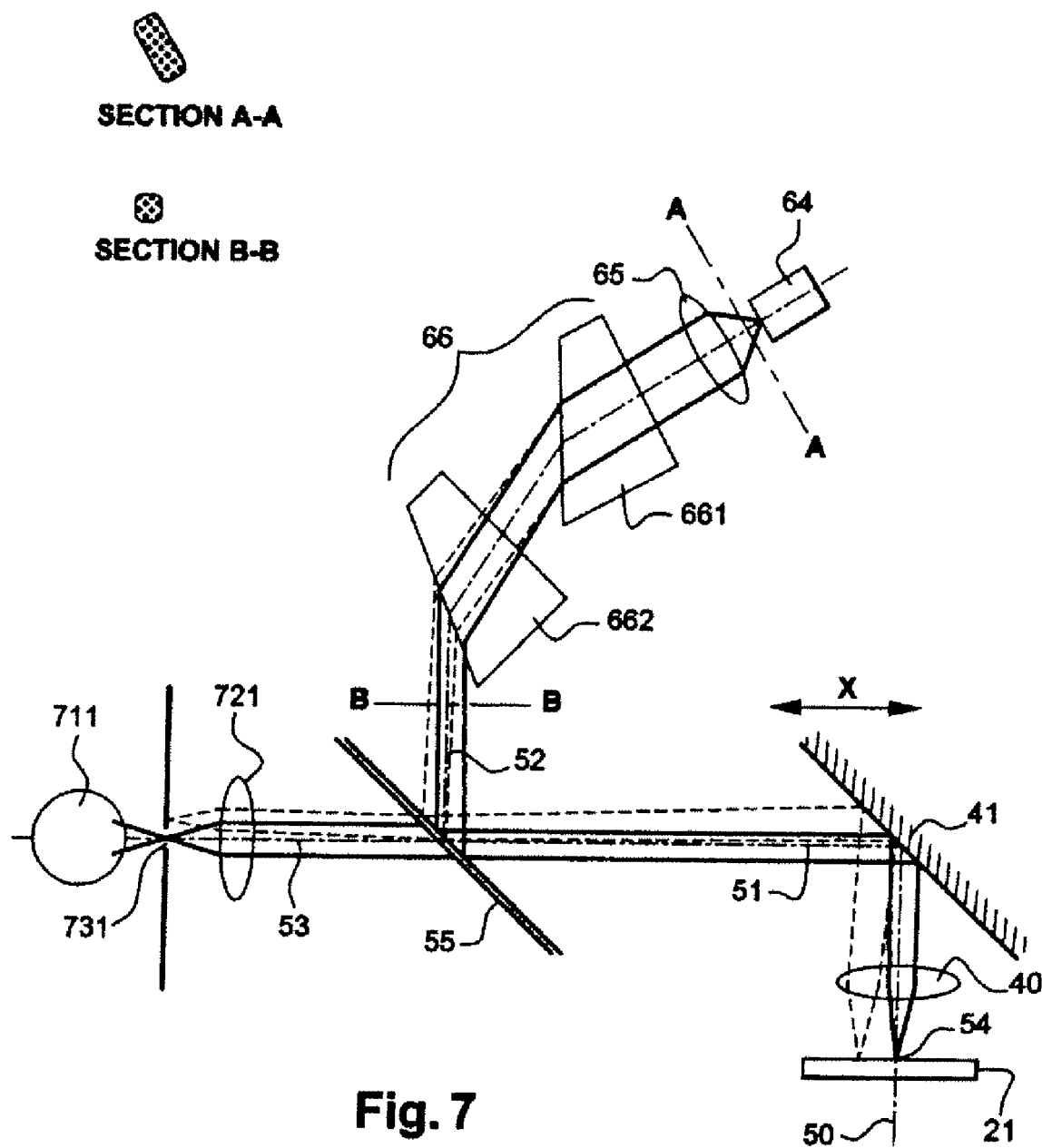
FIG. 7: principle of the means for separating wavelengths focused on the surface of the biochip. The detail a) shows a section through the light beam before passing through the anamorphoser device and the detail b) shows a section through the same light beam after passing through the anamorphoser device.

A first optical device 65, typically a group of lenses, converges the strongly divergent light beam from the laser diode 64 into an approximately parallel beam. The output beam of said first optical device 65 has, due to the very different apertures depending on the emission plane considered of the diode, an elongated, roughly rectangular, cross section, illustrated in the detail a) of FIG. 7. A second optical anamorphoser device 66 capable of shaping the beam so that it has a regular cross section, for example approximately square as illustrated in the detail b) of FIG. 7, is placed in the path of the light beam at the output from the first optical device 65. Furthermore, said second optical device 66 spreads the spectrum of the light of the beam, i.e. the various wavelengths present in the spectrum of the light beam emitted by the laser diode 64 have different directions at the output of said optical anamorphoser device 66.

This second optical device 66 is produced, for example, by using at least one anamorphic prism 661, 662, made of a material that is transparent to the light emitted by the diode 64, comprising at least two opposed parallel faces and at least two opposed faces forming an angle, the direction of which normal to the parallel faces is oriented according to the smallest dimension of the section of the light beam at the output of the first optical device 65.

Said at least one anamorphic prism 661, 662 is in addition oriented such that the light beam arrives approximately perpendicular to one of the faces forming an angle with the opposite face. Due to the refractive index of the material used to produce the prism, the beam is deflected in the plane parallel to the parallel faces of the prism 661, 662 and has, on exiting the opposite face, a cross section of unchanged width in the direction perpendicular to the parallel faces and of reduced width in the direction parallel to the parallel faces. Moreover, as the refractive index varies approximately as a function of the wavelength, the general case for transparent materials except for expensive low-dispersion glasses, the angle of deflection caused by the prism 661, 662 and hence the direction of the light at the output from the prism is different depending on the wavelength.

In one embodiment of the optical anamorphoser device 66, in order to accentuate the two effects of anamorphosing the beam and of wavelength-dependent dispersion, the optical beam passes in succession through at least two prisms 661, 662 so as to attain the desired effect on the cross section of the beam. In such an embodiment with at least two prisms 661, 662, in contrast to current use which arranges the prisms in opposite orientations to reduce chromatic aberration, the prisms 661, 662 are arranged in the same direction to increase the spreading of the spectrum.

On exiting the second optical anamorphoser device 66, the optical beam with the direction 52 that corresponds to the direction, shown in continuous lines in FIG. 7, of the light with the wavelength that characterizes the peak power emission of the diode 64 is directed along the optical axis 52 toward filtering means 55, for example a dichroic filter, that will direct the light corresponding to the desired wavelengths of the light to illuminate the chip 21 and stimulate the fluorescence onto the optical axis 51 in the direction of the carriage 30 of the rapid scanning along X. These filtering means 55 transmit the light having wavelengths corresponding to the fluorescence without significant reflection.

The light coming from the chip 21 that passes through the objective 40 of the confocal microscope follows a reversed optical path through to the filtering means 55, which act once again by reflecting the light centered on the emission wavelength of the diode 64 and by transmitting the light centered on the wavelength of the fluorescence along an optical axis 53 in the direction of the measurement means 70.

The measurement means 70 comprise at least one detector 711, 712, for example a photomultiplier, which receives the light coming from the chip 21 after passing through the filtering means 55.

In a manner known in a confocal microscope system, the light passes through an optical focusing device 721 which converges the optical beam onto the opening of a pinhole 731 before reaching the detector 711.

In the present device, the light emitted by the laser diode 64 passes through the second optical anamorphoser device 66, is reflected by the filtering means 55, and is then firstly focused at the surface of the chip 21. The various wavelengths emitted by the laser diode that is not perfectly monochromatic, for those which are sent toward the carriage 30 by the filtering means 55, having appreciably different directions, illustrated by dotted lines in FIG. 7, will converge on different points at the surface of the chip 21 after passing through the objective 40.

Advantageously, the various optical devices are oriented so that the light having the wavelength that corresponds to the peak luminous intensity of the diode 64 converge at the surface of the chip approximately on the axis of the objective 40.

The area of the chip illuminated in this way, essentially the most strongly illuminated area, i.e. that receiving the light having the wavelength that corresponds to the peak luminous intensity of the diode 64, emits a fluorescence having a wavelength shifted in relation to that of said peak luminous intensity.

Furthermore, the surface of the chip 21 reflects part of the light from the diode 64 which arrives at its surface. This reflected light comprises the various wavelengths that reach the surface of the chip 21 and which are focused by the objective 40 at various distances from the optical axis 50 of the objective depending on their wavelength, due to their different orientations after passing through the anamorphoser device 66. Collected by the objective 40 at the same time as the fluorescence light, this reflected light is directed onto the filtering means 55. The light having wavelengths close to the emission peak of the laser diode 64 is deflected by the filtering means 55 and that having wavelengths close to the fluorescence is transmitted in the direction of the measurement means 70.

However, due to the limited performance of the filtering means 55, part of the light reflected by the surface of the chip 21 which does not correspond to fluorescence, in particular the reflected light having a wavelength close to that of the fluorescence light, is transmitted in the direction of the measurement means 70.

As this light reflected and transmitted toward the measurement means has not come from the fluorescence, it comes from points on the chip 21 offset in relation to those from which the fluorescence light has come, situated close to the focal point 54 on the axis 50 of the objective 40.

This part of the reflected light that reaches through to the measurement means 70 corresponds to intermediate wavelengths between that of the emission peak of the laser diode 64 and that of the fluorescence, close enough to the wavelength of the emission peak of the diode 64 to have been sent from the illumination means 60 toward the objective 40 by the filtering means 55, and not far enough from the fluorescence wavelength to have been stopped by said filtering means 55. Although of a much weaker intensity than that of the emission peak of the laser diode 64, the intensity of this reflected light which is transmitted by the filter 55 is likely to disturb the fluorescence measurement.

However, due to its offset origin at the surface of the chip 21 in relation to the focal point 54, this reflected light is focused by the means 721 to a point offset in relation to the opening 731 of the pinhole and therefore does not reach the detector 711.

Hence, by using conventional prisms and the particularities of the confocal microscope, very good spectral filtering and fluorescence images of the chip with a high signal-noise ratio are obtained without expensive means.

In a known manner, when several illumination wavelengths are used and several fluorescence wavelengths are observed, the illumination means 60 and the measurement means 70 comprise different light sources and different sensors dedicated to the different wavelengths that are directed from the sources and toward the sensors by traditional optical means, for example filters. It is quite obvious that the principles described for the case of one source using a laser diode are applicable to any means of measurement employing a luminous emission source having an emission spectrum likely to interfere with the fluorescence signal.

Figure 8:
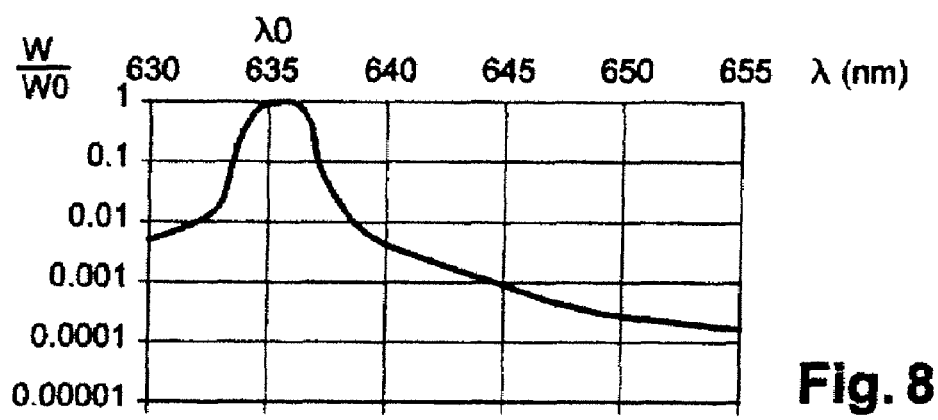
FIG. 8: example of the distribution of the luminous power as a function of wavelength for a red laser diode.

In one embodiment of the device according to the disclosed embodiments, a red laser diode 64 is used the emission of which is centered on 635 nanometers and which is designed to illuminate Cy5 dyes. This diode 64 has an emission spectrum the power W of which as a function of the wavelength $\lambda$ is of the type shown in FIG. 8. Its residual energy at the wavelength of 650 nanometers is relatively high, at a level of around $10^{-3}$ to $10^{-4}$ times that of the emission peak, with regard to the sensitivity of the detection means 70 used by the confocal microscope. When passing through the optical anamorphoser device 66 the radiation corresponding to the wavelength of 650 nanometers has a direction appreciably different from that corresponding to the emission peak at 635 nanometers.

Figure 9:
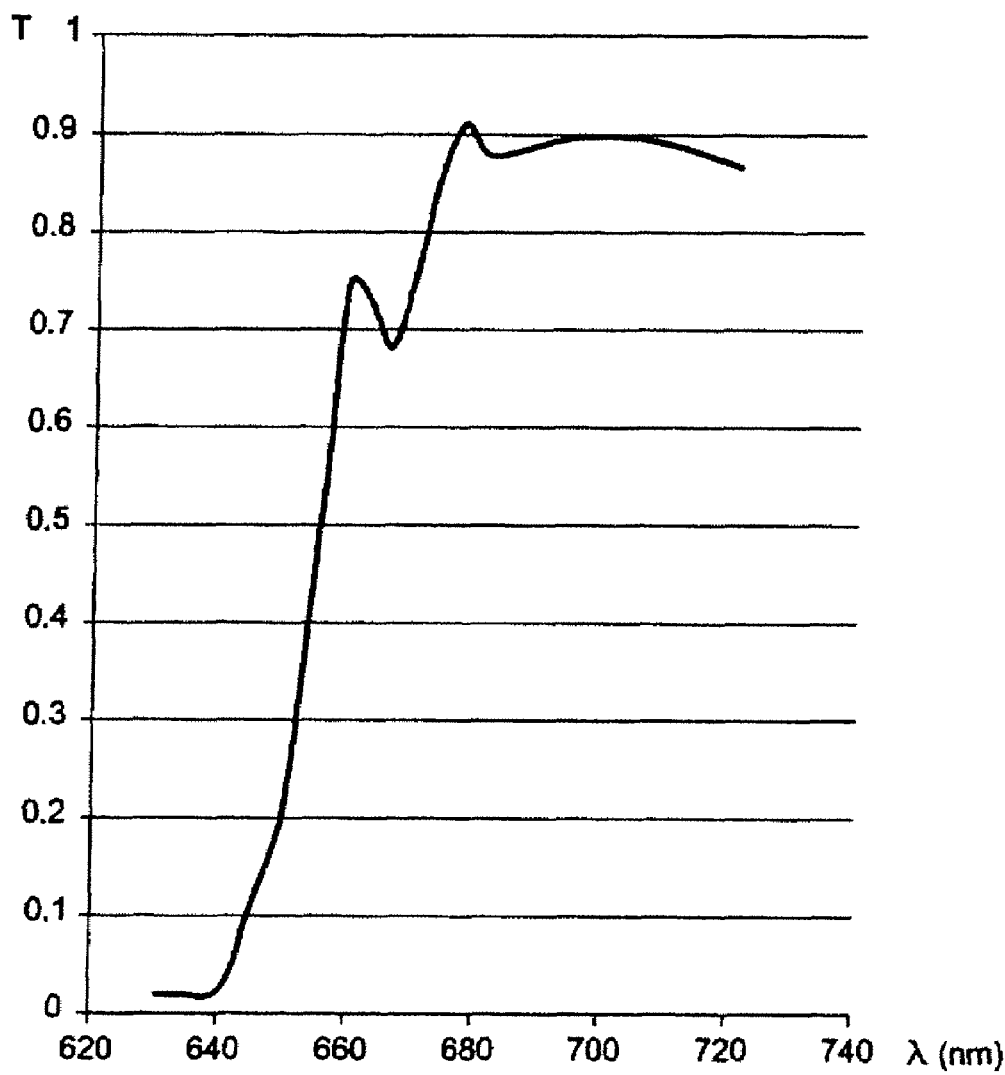
FIG. 9: example of the characteristic curve of a dichroic filter for red colors.

A high-pass dichroic filter 55 inclined at 45° to the direction 52 of the optical beam exiting the illumination means 60 acts as a filtering means. This dichroic filter 55, for which an example of the characteristic curve of the transmission rate $\tau$ as a function of the wavelength is given in FIG. 9, with a slope situated around 650 nanometers, reflects the light having a wavelength $\lambda$ less that 650 nanometers, in particular light at the wavelength $\lambda_0$=635 nanometers of the emission peak of the diode 64 which is pointed at 90°, in the direction of the rapid scanning system along X and of the objective 40 of the microscope. This dichroic filter 55 allows the light coming from the diode 64 with a wavelength greater than 650 nanometers which is not sent toward the chip to pass through.

This light freed of wavelengths greater than 650 nanometers and the direction of which varies depending on the wavelength provides, after passing through the objective 40 of the microscope, an area of the biochip that is weakly illuminated at the wavelength of 650 nanometers offset by around 40 micrometers in relation to the area strongly illuminated at the wavelength $\lambda_0$ of 635 nanometers, which is preferably positioned on the axis 50 of the objective.

As the resolution of the confocal microscope is 10 micrometers at the surface of the chip, the area illuminated at 650 nanometers is therefore offset in relation to the axis 50 of the objective by several times the resolution of the analysis device.

In the immediate proximity of the axis 50 of the objective, the chip emits fluorescence light centered on a wavelength of 670 nanometers, the characteristic emission of Cy5 dyes, the source of which is concentrated over the surface strongly illuminated by the light corresponding to the intensity peak of the laser diode at 635 nanometers and close to the axis 50 of the objective, and reflected light having a wavelength that is further from 635 nanometers the greater the distance from the axis 50 of the microscope objective.

As the surface of the chip is located approximately in the focal plane of the objective 40, the fluorescence light and the reflected light provide, after passing through the objective, a parallel optical beam which is once again directed toward the dichroic filter 55, following the reverse path of the light emitted by the laser diode 64. Wavelengths of light lower than 650 nanometers are once again deflected by 90° by the dichroic filter, while wavelengths greater than 650 nanometers are transmitted toward the detection means 70. The convergent optical device 721 situated in front of the pinhole generates an image of the focal plane of the objective 40. At the point of the image corresponding to the patch of fluorescence centered on a wavelength of 670 nanometers, close to the optical axis 50 of the microscope objective, the pinhole opening 731 allows the fluorescence light to pass through, the intensity of which is measured by the photomultiplier 711 situated behind the pinhole opening 731. The other points of the image, which correspond to light reflected by the surface of the chip with a wavelength greater than 650 nanometers, which are not stopped by the dichroic filter 55, are offset in relation to the pinhole opening 731 and do not therefore influence the measurement carried out by the photomultiplier 711.

The invention claimed is:

1. A scanning imaging device for scanning a surface of a sample comprising:
    optical means for determining a focal point;
        a first device for displacing the focal point in a rapid scanning movement in a direction X approximately parallel to the surface of the sample, in order to describe at least one scanning line along the X direction at the surface of the sample;
        a movable support on which the sample is fixed; and
        a second device for displacing said movable support in a direction Y, approximately parallel to the surface of the sample and approximately perpendicular to the rapid scanning direction X;
    wherein the movable support rests on at least one guiding column in the Y direction that leaves said movable support free to move in a Z direction approximately perpendicular to a plane defined by the X and Y directions,
    the second device comprising:
        at least one first actuator, the action of which displaces the movable support in relation to the optical means in the Z direction such that the scanning line along the X direction is shifted approximately uniformly in the Z direction; and
        at least one second actuator, the action of which modifies an inclination of the movable support in such a way that the scanning line along the X direction is essentially inclined in a plane defined by the X and Z directions by rotation about a rotation axis a position of which varies depending on a position of the movable support along the Y direction and/or depending on a position determined by the first actuator of the movable support in the Z direction.

2. The device as claimed in claim 1, further comprising a focus control device configured to generate a focal point position error signal which, in response to said error signal, during the rapid scanning movement along the X direction, controls the first actuator to correct the position of the surface of the sample in relation to the focal point through modifications to the position in the Z direction of the scanning line at the surface of the sample.

3. The device as claimed in claim 2, wherein, in response to the error signal, the focus control device controls the second actuator during the rapid scanning movement along the X direction to change the inclination of the scanning line along the X direction.

4. The device as claimed in claim 3, wherein the focus control device controls the second actuator to modify the inclination of the scanning line along the X direction, at a lower frequency than a frequency at which the first actuator is controlled to correct the Z position of said scanning line along the X direction.

5. The device as claimed in claim 1, wherein at least one of the first actuator and the second actuator comprises at least one height roller and at least one roll roller, each having an axis of rotation approximately perpendicular to the Z direction and having a position of said axis of rotation capable of being modified along the Z direction by a motor.

6. The device as claimed in claim 5, wherein at least one of the height roller and the roll roller is mounted on an eccentric shaft rotationally driven by their respective motors to modify the Z position of the at least one of the height roller and the roll roller.

7. The device as claimed in claim 1, wherein the first actuator acts at a point of action lying approximately in a plane defined by the X and Z directions and by the scanning line along the X direction.

8. The device as claimed in claim 1, wherein the first actuator acts at a first point of action applied to one face of the movable support.

9. The device as claimed in claim 8, wherein the first point of action lies approximately on the axis of the sample in the Y direction.

10. The device as claimed in claim 9, wherein the second actuator acts through a displacement in the Z direction of a second point of action applied to one face of the movable support and offset in the X direction in relation to the first point of action.

11. The device as claimed in claim 8, comprising a fixed or adjustable support element on which the movable support rests, said support element being offset in the Y direction in relation to a line passing through the first and second points of action wherein said support element, together with the first point of action determines the rotation axis.

12. The device as claimed in claim 1, wherein the first actuator acts through a displacement in the Z direction of a third point of action applied to one face of a guiding structure on which the movable support is movable in the Y direction.

13. The device as claimed in claim 12, wherein the second actuator acts through a displacement in the Z direction of a fourth point of action applied to one face of the movable support, said fourth point of action being offset in the X direction in relation to a guiding column of the movable support, said guiding column being joined to the guiding structure and configured to allow rotation of the movable support about an axis approximately parallel to the Y direction.

14. The device as claimed in claim 1, comprising a confocal microscope for observing the surface of the sample.

15. The device as claimed in claim 1, wherein the rapid scanning movement in the X direction is obtained by a displacement along a linear path of the optical means.

16. The device as claimed in claim 15, wherein the rapid scanning movement in the X direction is a reciprocating movement in which the optical means are driven by a rotating motor and a connecting rod joined in an offset manner to an output shaft of said motor.

17. The device as claimed in claim 1, wherein the image of the surface of the sample is observed by stimulating the fluorescence of the sample.

18. The device as claimed in claim 17, wherein the fluorescence is stimulated by at least one light source emitting a spectrum of light having an intensity peak centered on a wavelength $\lambda_0$ shifted in relation to the fluorescence wavelength, said device comprising:

an optical dispersion means for guiding the light radiation corresponding to the various wavelengths emitted by the light source in different directions;

an optical means for causing radiation from the light source corresponding to the wavelength $\lambda_0$ to converge on the focal point;

a confocal microscope for observing the fluorescence emitted by the surface of the sample comprising at least one pinhole through the opening of which the light received by a photon sensor passes, said confocal microscope being set up so that the light coming from the surface of the sample close to the focal point, emitted by fluorescence, arrives at the pinhole opening and so that the light emitted by the source at wavelengths shifted in relation to $\lambda_0$ close to the wavelength of the fluorescence light, and reflected by the surface of the sample, from points on the surface of the sample offset in relation to the focal point, arrive alongside the pinhole opening and do not reach the photon sensor.

19. The device as claimed in claim 18, wherein the optical dispersion means is set up to obtain anamorphosis of the light radiation emitted by the light source.

\* \* \* \* \*